(12) United States Patent
Xu

(10) Patent No.: US 8,828,968 B2
(45) Date of Patent: Sep. 9, 2014

(54) NANOPARTICLE OF GLUCIDAMIN FOR TREATING TUMOR AND PREPARATION METHOD THEREOF

(75) Inventor: Zirong Xu, Zhejiang (CN)

(73) Assignee: Ningbo Puai Bioengineering Co., Ltd., Ningbo (CN)

( * ) Notice: Subject to any disclaimer, the term of this patent is extended or adjusted under 35 U.S.C. 154(b) by 800 days.

(21) Appl. No.: 12/523,220

(22) PCT Filed: May 22, 2007

(86) PCT No.: PCT/CN2007/070043
§ 371 (c)(1),
(2), (4) Date: Nov. 16, 2009

(87) PCT Pub. No.: WO2008/089628
PCT Pub. Date: Jul. 31, 2008

(65) Prior Publication Data
US 2010/0069324 A1    Mar. 18, 2010

(30) Foreign Application Priority Data
Jan. 18, 2007   (CN) .......................... 2007 1 0066758

(51) Int. Cl.
| | | |
|---|---|---|
| *A61K 31/715* | (2006.01) | |
| *A61K 31/722* | (2006.01) | |
| *C07H 5/04* | (2006.01) | |
| *C07H 5/06* | (2006.01) | |
| *C08B 37/08* | (2006.01) | |
| *C08B 37/00* | (2006.01) | |
| *A61K 31/7135* | (2006.01) | |
| *A61K 9/14* | (2006.01) | |
| *A61K 31/726* | (2006.01) | |

(52) U.S. Cl.
CPC .............. *A61K 31/7135* (2013.01); *A61K 9/14* (2013.01); *A61K 31/726* (2013.01)
USPC ................ 514/54; 514/55; 536/55.1; 536/20; 536/18.7

(58) Field of Classification Search
USPC ........................ 536/55.1, 20, 18.7; 514/54, 55
See application file for complete search history.

(56) References Cited

FOREIGN PATENT DOCUMENTS

| CN | 1559433 A | * | 1/2005 |
|---|---|---|---|
| CN | 1559614 A | * | 1/2005 |
| CN | 1685829 A | | 10/2005 |
| CN | 1685831 A | | 10/2005 |

OTHER PUBLICATIONS

Caihong et al., CN 1559614 A; Jan. 5, 2005 (English Machine Translation).*
Caihong et al., CN 15594333 A; Jan. 5, 2005 (English Machine Translation).*
Trisha Gura's ; Science, Nov. 1997, pp. 1041-1042.*
International Search Report of PCT/CN2007/070043, dated Nov. 1, 2007.
Shen et al. "Research Progress on Pharmacology of Glucidamin." Shanghai Medical & Pharmaceutical Journal. vol. 6, No. 6, 2001, pp. 268-270, Abstract.

* cited by examiner

*Primary Examiner* — Shaojia Anna Jiang
*Assistant Examiner* — Michael C Henry
(74) *Attorney, Agent, or Firm* — Hamre, Schumann, Mueller & Larson, P.C.

(57) ABSTRACT

A nanoparticle of glucidamin derived from organism for treating tumor and preparation method thereof, wherein the viscosity-average molecular weight of glucidamin is in the range of $1\times10^3$-$9\times10^5$, and the amount of free amino groups in the glucidamin is in the range of 50%-100% based on the total amino groups. The preparation method of the nanoparticle comprises steps listed below: (1) adding the glucidamin possessing one or more molecular weight into thin acid solution at 20-60° C. to form saccharan solution, wherein the content of saccharan in solution is in the range of 0.1%-5% by weight; (2) adjusting the pH of the solution to 6-9 in order to form emulsion of microparticle; (3) separating the microparticle from the emulsion, dried at low temperature to obtain the nanoparticle of glucidamin for treating tumor. The nano-class glucidamin can enhance their activity against tumor. The particle diameter of glucidamin nanoparticle prepared by the method disclosed in the present invention exhibits homogeneous distribution, meanwhile, the nanoparticle is easy to be separated and purified.

9 Claims, 3 Drawing Sheets

NANOPARTICLE OF GLUCIDAMIN FOR TREATING TUMOR AND PREPARATION METHOD THEREOF

TECHNICAL ART

The invention relates to a nanoparticle for treating tumor, more particularly, a nanoparticle of glucidamin for treating tumor and preparation method thereof.

BACKGROUND ART

Glucidamin (amino polysaccharide) is a natural macromolecule polymer, the degradation product of which is an amino monosaccharide. It won't be toxic or harmful toward human tissue, and possesses anti-tumor activity and bacteriostatic action. The glucidamin microsphere has been used in controlled release system of medicine. The methods for preparing the glucidamin microsphere include water-oil two-phase process, emulsion technology and spray drying method, etc. Generally, these methods are complicated and need organic solvents and surfactant. Therefore, consideration of safety exists in the saccharan microsphere produced.

Some researches demonstrate that the glucidamin may act on some tumor cells directly, disturb the cell metabolism, inhibit the cell growth and induce apoptosis of tumor cells by some pathways which have not been elucidated. Additionally, it is reported that the glucidamin is capable of inhibiting the growth of vascular endothelial cell, restricting the tumor growth and blocking the adhesion of vascular endothelial cell adhesion molecule so as to restrict the metastasis of tumor cells. Moreover, some researches found that the glucidamin is capable of activating immunocytes, such as macrophage, lymphocyte, NK cell, and the complement system, inducing the production of manifold cytokines and improving immunity of organism, so as to exert anti-tumor action.

Some researches found that some metal ions, such as zinc, cobalt and copper, possess superior anti-tumor activity. Composite materials produced by loading such metal ions on degradable biocompatible polysaccharide microparticles (or nanoparticles) possess not only superior anti-tumor activity, but also some advantages, such as extended release, prolonged action and non-residue.

CONTENTS OF THE INVENTION

The major purpose of the invention is to provide a nanoparticle of glucidamin and preparation method thereof for overcoming the defects in the prior art.

According to the present invention, the technical problems said above are solved by the following technical solutions.

A nanoparticle of glucidamin for treating tumor, which is derived from glucidamin from organism, wherein the viscosity-average molecular weight of said glucidamin is in the range of $1\times10^3$-$9\times10^5$, and the amount of free amino groups in the glucidamin is in the range of 50%-100% based on the total amino groups.

Preferably, the particle diameter of said nanoparticle of glucidamin for treating tumor is in the range of 5~500 nm.

Preferably, said nanoparticle of glucidamin for treating tumor is a nanoparticle of glucidamin loaded with metal ions, wherein the viscosity-average molecular weight of glucidamin is in the range of $1\times10^3$-$9\times10^5$, the amount of free amino groups in the glucidamin is in the range of 50%-100% based on the total amino groups, and the content of the metal ions is in the range of 1-20% by weight.

The method for preparing the nanoparticle of glucidamin for treating tumor comprises the following steps:

(1) adding the glucidamins having one or more molecular weight into a diluted acid solution at 20-60° C. to form a saccharan solution, wherein the content of saccharan in the solution is in the range of 0.1%-5% by weight;

(2) adjusting the pH of the solution to 6-9 in order to form emulsion of microparticle;

(3) separating the microparticle from the emulsion, dried at low temperature to obtain the nanoparticle of glucidamin for treating tumor.

Preferably, the method for preparing said nanoparticle of glucidamin loaded with metal ion comprises the following steps:

(1) adding the glucidamins into a diluted acid solution at 20-60° C. to form a saccharan solution, wherein the viscosity-average molecular weight of said glucidamin is in the range of $1\times10^3$-$9\times10^5$, and the content of saccharan in the solution is in the range of 0.1%-5% by weight;

(2) adjusting the pH of the solution to 3-8 in order to form emulsion of microparticles;

(3) separating the microparticles from the emulsion, washed to neutral pH, adding the microparticles into the solution of metal ion the concentration of which is in the range of 100~1000 mg/L; then, shaking the system to let the microparticles adsorb the ions, drying, and obtaining the nanoparticle of glucidamin loaded with metal ions.

Preferably, said diluted acid solution is acetic acid or hydrochloric acid.

Preferably, said solution of metal ion is at least one solution of sulphate, hydrochloride or nitrate of said metal ion.

Compared with the prior art, the advantageous effects of the invention are:

(1) The anti-tumor activity of glucidamin could be improved greatly by preparing it into nanoparticles or nanoparticles loaded with metal ions, and said nanoparticles can be used broadly as anti-tumor medicine.

(2) The invention provides a method for preparing a nanoparticle of glucidamin for treating tumor under mild condition (i.e., normal temperature and normal pressure). The particle diameter of the glucidamin nanoparticle and the glucidamin nanoparticle loaded with metal ions prepared according to the present method exhibits uniform distribution. Meanwhile, said nanoparticle can be easily isolated and purified, and won't incur safety problem, which is in favor of the safety and quality control when developing them into anti-tumor medicine.

In the figures: a. gastric cancer cell untreated; b. gastric cancer cell treated with the nanoparticle of glucidamin; c. hepatoma carcinoma cell untreated; d. hepatoma carcinoma cell treated with the nanoparticle of glucidamin loaded with copper; e. hepatoma carcinoma cell untreated; f. hepatoma carcinoma cell treated with the nanoparticle of glucidamin.

MODE OF CARRYING OUT THE INVENTION

The present invention will be illustrated in the following referring to the specific examples. In the following examples, all the percentage of solution is based on weight/volume, unless stated otherwise.

EXAMPLE 1

Figure 1:
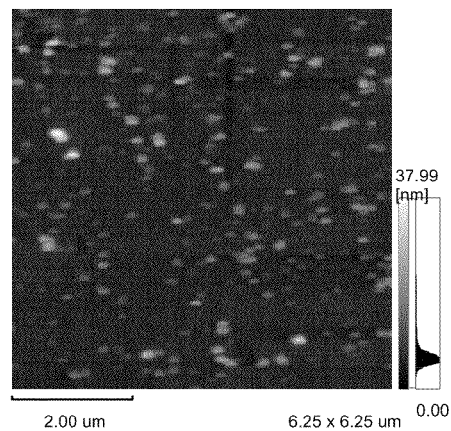
FIG. 1 is the image of the nanoparticle of glucidamin prepared in example 1 observed by atomic force microscope.

Glucidamin is added into 0.5% acetic acid solution at 20° C. to form a 0.1% saccharan solution, wherein the viscosity-average molecular weight (Mr) of the glucidamin is $1.8 \times 10^4$. The pH of the solution is adjusted to 4.0 in order to form emulsion of microparticles. The emulsion is centrifuged at 3000 rpm/min. The precipitate is washed with distilled water to neutral pH, then cryodried to obtain the nanoparticle of glucidamin. Observed by atomic force microscope, the nanoparticles prepared by the method said above have relatively regular globular structure (see FIG. 1), which can be stably stored under pH 3-8.

EXAMPLE 2

Glucidamin is added into 1% hydrochloric acid solution at 30° C. to form a 2% saccharan solution, wherein the viscosity-average molecular weight (Mr) of the glucidamin is $4.7 \times 10^3$. The pH of the solution is adjusted to 6.0 in order to form emulsion of microparticles. The emulsion is precipitated and the precipitate is washed with distilled water to neutral pH. Then, the precipitate is cryodried to obtain the nanoparticle of glucidamin.

Figure 2:
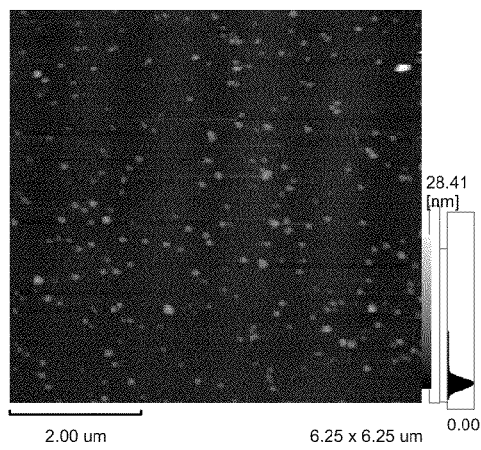
FIG. 2 is the image of the nanoparticle of glucidamin prepared in example 2 observed by atomic force microscope.

Observed by the atomic force microscope, the nanoparticles prepared by the method said above have globular structure (see FIG. 2), which can be stably stored under pH 3-8.

EXAMPLE 3

Glucidamin is added into 0.5% acetic acid solution at 60° C. to form a 5% saccharan solution, wherein the viscosity-average molecular weight (Mr) of the glucidamin is $5.2 \times 10^4$. The pH of the solution is adjusted to 6.5 in order to form emulsion of microparticles. The emulsion is centrifuged at 4000 rpm/min for precipitation and isolation. The precipitate is washed with distilled water to neutral pH and dried to obtain the microparticle of saccharan. The dry powder of saccharan is added into a 500 mg/L cobalt ion solution. Shaking the system at 300 rpm/min to let the powder absorb the ions (30 min-24 hours). After completion of absorption, the microparticles of glucidamin are dried to obtain the nanoparticles of glucidamin loaded with cobalt.

Figure 3:
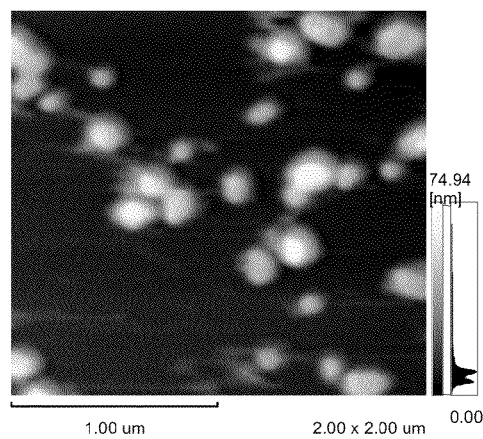
FIG. 3 is the image of the nanoparticle of glucidamin loaded with cobalt prepared in example 3 observed by atomic force microscope.

The content of cobalt in the nanoparticle loaded with cobalt prepared according to the above method is about 10%. Observed by the atomic force microscope, the nanoparticles have relatively regular globular structure (see FIG. 3), which can be stably stored under pH 3-8.

EXAMPLE 4

Glucidamin is added into 0.5% acetic acid solution at 25° C. to form a 1% saccharan solution, wherein the viscosity-average molecular weight (Mr) of the glucidamin is $1.1 \times 10^4$. The pH of the solution is adjusted to 6 in order to form emulsion of microparticles. The emulsion is centrifuged at 4000 rpm/min for precipitation and isolation. The precipitate is washed with distilled water to neutral pH and dried to obtain the microparticle of saccharan. The dry powder of glucidamin is added into a 600 mg/L copper ion solution. Shaking the system at 300 rpm/min to let the powder absorb the ions (30 min-24 hours). After the absorption is completed, the microparticles of saccharan are dried to obtain the nanoparticles of glucidamin loaded with copper.

Figure 4:
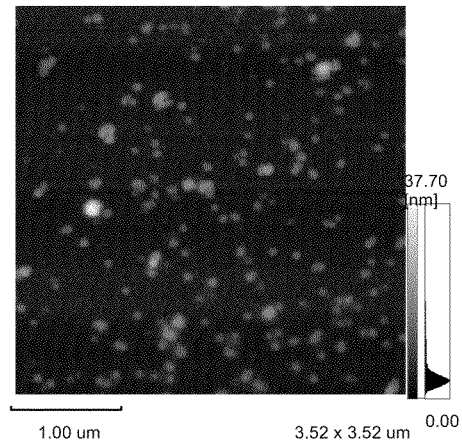
FIG. 4 is the image of the nanoparticle of glucidamin loaded with copper prepared in example 4 observed by atomic force microscope.

The content of copper in the nanoparticle of glucidamin loaded with copper prepared according to the method said above is about 20%. Observed by the atomic force microscope, the nanoparticles have relatively regular globular structure (see FIG. 4), which can be stably stored under pH 3-8.

EXAMPLE 5

Glucidamin is added into 0.5% acetic acid solution at 30° C. to form a 2% saccharan solution, wherein the viscosity-average molecular weight (Mr) of the glucidamin is $8.3 \times 10^3$. The pH of the solution is adjusted to 7 in order to form emulsion of microparticles. The emulsion is centrifuged at 6000 rpm/min for precipitation and isolation. The precipitate is washed with distilled water to neutral pH and dried to obtain the microparticle of saccharan. The dry powder of glucidamin is added into a 800 mg/L zinc ion solution. Shaking the system at 400 rpm/min to let the powder absorb the ions (30 min-24 hours). After the absorption is completed, the microparticles of glucidamin are dried to obtain the nanoparticles of glucidamin loaded with zinc.

Figure 5:
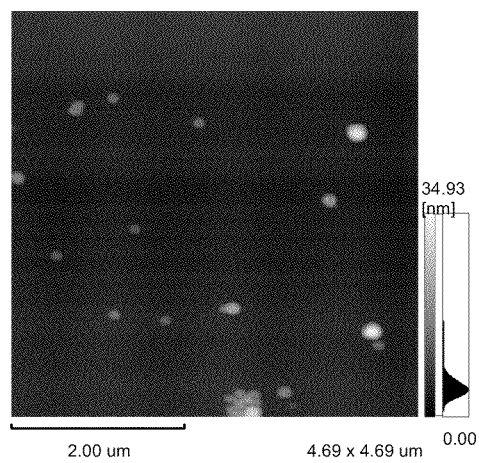
FIG. 5 is the image of the nanoparticle of glucidamin loaded with zinc prepared in example 5 observed by atomic force microscope.

The content of zinc ion in the nanoparticle of glucidamin loaded with zinc prepared according to the method said above is about 8%. Observed by the atomic force microscope, the nanoparticles of glucidamin have good shape (see FIG. 5), which can be stably stored under pH 3-8.

EXAMPLE 6

Figure 6:
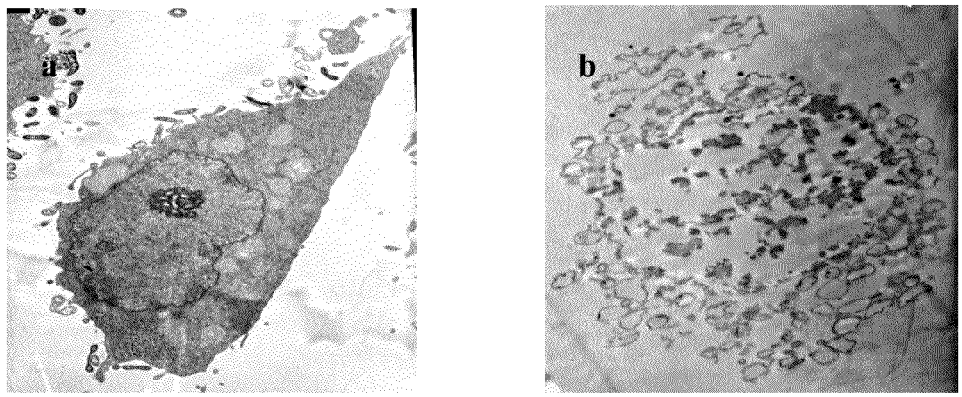
FIG. 6 is the image of gastric cancer cells after being treated with the nanoparticle of glucidamin for 24 hours in example 6 observed by transmission electron microscope.

Gastric cancer cells are treated with the nanoparticle of glucidamin for 24 hours, fixed with 10% glutaraldehyde and washed with 0.1 M phosphate buffer for 3 times. 1% osmic acid is added. 2 hours later, gradient infiltration is performed using acetone plus Epon812. The cells are embedded in Epon812 epoxy resin in situ, sliced by LKB ultramicrotome, double-stained by uranyl acetate and lead citrate, and observed by transmission electron microscope (model JEM-1200EX). According to FIG. 6, for the cells in the control group (FIG. 6a), the surface of the cellular membrane is covered with microvillus, the structure of the cellular membrane is compact, the organelles are normal, the mitochondrions are round or elliptical, cristae is clear, the karyotheca is complete, and the chromatin is distributed uniformly. After treatment with the nanoparticles of glucidamin for 24 hours, the shape of cells indicates cell necrosis, and the cells have been broken into cell debris.

EXAMPLE 7

Hepatoma carcinoma cells BEL7402 are innoculated into cell culture flask. After adherent culture for 24 hours, the emulsion of nanoparticles of glucidamin for treating tumor is added. After treatment for 24 hours, the culture fluid is discarded. The cells in the culture flask are digested by trypsin, collected, fixed with 10% glutaraldehyde and washed with 0.1 M phosphate buffer for 3 times. 1% osmic acid is added. 2 hours later, gradient infiltration is performed using acetone plus Epon812. The cells are embedded in Epon812 epoxy resin in situ, sliced by LKB ultramicrotome, double-stained by uranyl acetate and lead citrate, and observed by transmission electron microscope (model JEM-1200EX). The result is shown in FIG. 7.

Figure 7:
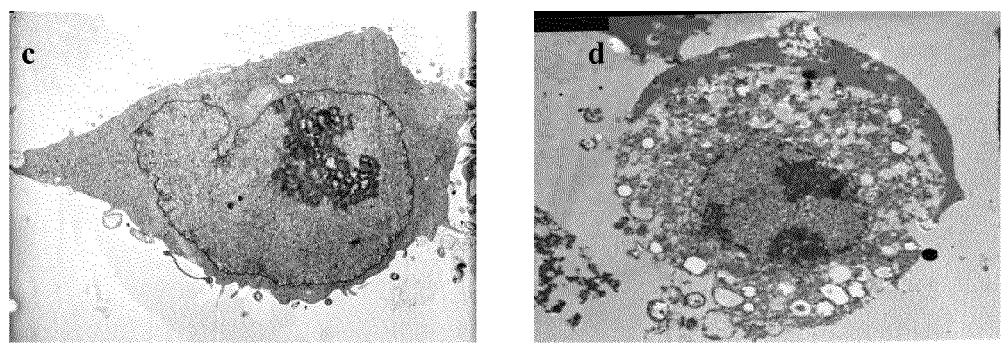
FIG. 7 is the image of hepatoma carcinoma cell after being treated with the nanoparticle of glucidamin for 24 hours in example 7 observed by transmission electron microscope.

According to FIG. 7, for the cells in the control group (FIG. 7c), the cell body is smooth, the surface of the cellular membrane is covered with microvillus, the organelles are normal, the mitochondrions are round or elliptical, cristae is clear, the karyotheca is complete, and the chromatin is distributed homogeneously. After treatment with the nanoparticles of glucidamin (see FIG. 7d), many vacuoles are contained in the cell, the cellular membrane is broken, the nuclear envelop disappear, most organelles are broken, the mitochondrions are swelling, the cell nuclei are concentrated, and the structure of nucleoli is converted from reticulation to circularity.

EXAMPLE 8

Figure 8:
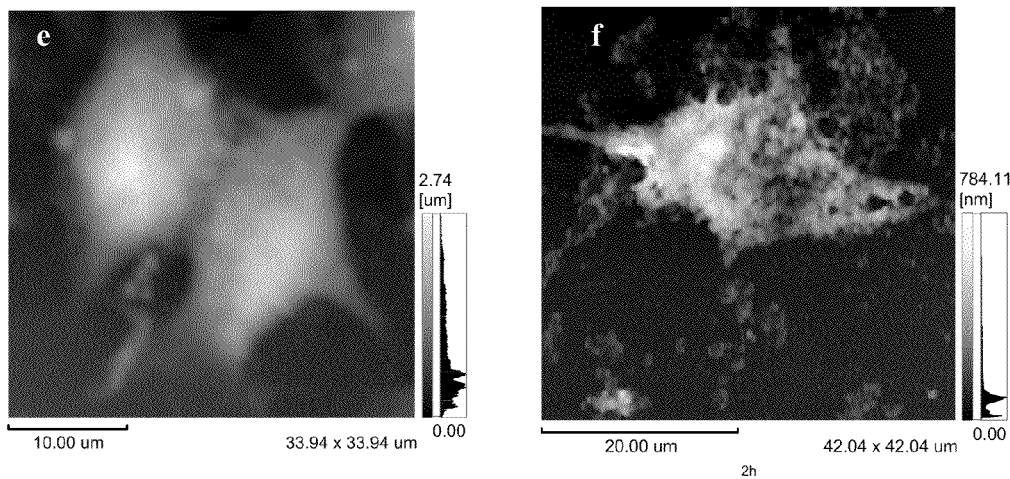
FIG. 8 is the image of hepatoma carcinoma cell after being treated with the nanoparticle of glucidamin loaded with copper for 2 hours in example 8 observed by transmission electron microscope.

Hepatoma carcinoma cells BEL7402 are incubated on the mica slice in 24-well plate for 24 hours. The emulsion of nanoparticles of glucidamin loaded with copper is added into the culture fluid, and incubated in the 5% $CO_2$ cell incubator for another 2 hours. The mixture is taken out, flushed with phosphate buffer for 3 times, fixed with 1.5% glutaraldehyde for 5 minutes, flushed with redistilled water for 3 times in order to eliminate the disturbance of the salts, dried in the air, and observed by atomic force microscope. According to FIG. 8, in the control group (FIG. 8e), the tumor cells show fusiform, the lamellar structure of the cellular membrane is complete, the edge is smooth, the nuclei bulge, the shape thereof corresponds to the cell body, the cytoplasm is uniform, the cells arrange regularly, and there is clear linker between adjacent cells. After treatment with the nanoparticles of glucidamin loaded with copper for 2 hours (see FIG. 8f), the surface of the cells becomes rough, collapsed and broken. Irregular tiny holes appear on the cell, the edge becomes uneven, the cellular membrane is dissolved, and the cell debris appear around the cell.

The invention also relates to the composition used as medicines for treating tumor, which is composed of the nanoparticles of glucidamin, the nanoparticles of glucidamin loaded with metal ions and pharmaceutically acceptable carriers. The composition could be made into a great variety of dosage forms if necessary. The suitable dosage may be determined by the physicians according to the following factors, such as the gender, age, weight and general condition of the patient as well as the mode of administration. Said tumor may be selected from: nasopharyngeal carcinoma, esophageal cancer, gastric cancer, cancer of intestine, hepatoma, lung cancer, bladder carcinoma, ovarian cancer, pancreatic cancer, breast carcinoma, renal carcinoma, prostatic carcinoma, brain tumor, leukemia or hysteromyoma.

The term "pharmaceutically acceptable" as used herein refers to the molecule or composition which won't produce disadvantageous, allergic or other untoward effects when suitably given to the animal or people. The term "pharmaceutically acceptable carriers" as used herein shall be compatible with the nanoparticles of glucidamin for treating tumor according to the invention, in other words, can be mixed with the nanoparticles while won't reduce the effects of the pharmaceutical composition greatly. The specific examples of the materials which can be used as pharmaceutically acceptable carriers or components are listed as follows: sugars (such as lactose, glucose and sucrose), starches (such as corn starch and potato starch), cellulose and the derivatives thereof (such as sodium carboxymethycellulose, ethyl cellulose and methyl cellulose), the powder of tragacanth, malt, gelatin, talc, solid lubricant (such as stearic acid and magnesium stearate), calcium sulphate, vegetable oil (such as peanut oil, cottonseed oil, sesame oil, olive oil, corn oil and cocoa oil), polyols (such as propylene glycol, glycerol, sorbitol, mannitol and polyethylene glycol), alginic acid, emulsifying agent (such as Tween), wetting agents (such as sodium lauryl sulphate), colorants, flavorants, tabletting agents, stabilizing agent, antioxidants, preservative, no-pyrogen water, isotonic saline solution and phosphate buffer, etc.

It should be noticed that only some specific embodiments are described in the above. Obviously, the present invention may not be limited to such embodiments, to which many modifications can be made. All the modifications which can be derived or thought of from the disclosure of the specification directly are intended to be within the scope of the present invention.

What is claimed is:

1. A preparation for treating gastric cancer or hepatoma, comprising nanoparticles of glucidamin and a pharmaceutically acceptable carrier, wherein said glucidamin is derived from an organism, a viscosity-average molecular weight of the glucidamin is in a range of $1 \times 10^3$-$9 \times 10^5$, and an amount of free amino groups in the glucidamin is in a range of 50%-100% based on the total amount of amino groups in the glucidamin, wherein the preparation includes the nanoparticles of glucidamin in an amount sufficient for treating gastric cancer or hepatoma in a subject in need thereof, and wherein the preparation is obtained by (1) adding the glucidamin into a diluted acid solution at 20-60° C. to form a polysaccharide solution, wherein an amount of the polysaccharide in the polysaccharide solution is in a range of 0.1%-5% by weight;

(2) adjusting a pH of the polysaccharide solution obtained in (1) to 6-9 in order to form an emulsion of microparticles; and (3) separating the microparticles from the emulsion obtained in (2), and (4) drying the separated microparticles obtained in (3) at low temperature to obtain the preparation.

2. The preparation as claimed in claim 1, wherein a particle diameter of each of said nanoparticles is in a range of 5-500 nm.

3. The preparation as claimed in claim 1, wherein said diluted acid solution is acetic acid or hydrochloric acid.

4. A preparation for treating gastric cancer or hepatoma, comprising nanoparticles of glucidamin and a pharmaceutically acceptable carrier, wherein the glucidamin is derived from an organism, a viscosity-average molecular weight of the glucidamin is in a range of $1 \times 10^3$-$9 \times 10^5$, and an amount of free amino groups in the glucidamin is in a range of 50%400% based on the total amount of amino groups in the glucidamin, wherein said nanoparticles of glucidamin are loaded with metal ions, and the content of the metal ions is in a range of 1-20% by weight, wherein the preparation includes the nanoparticles of glucidamin in an amount sufficient for treating gastric cancer or hepatoma in a subject in need thereof, and wherein the preparation is obtained by (1) adding the glucidamin into a diluted acid solution at 20-60° C. to form a polysaccharide solution, wherein an amount of the polysaccharide in the polysaccharide solution is in a range of 0.1%-5% by weight;
(2) adjusting a pH of the polysaccharide solution obtained in (1) to 3-8 so as to form an emulsion of microparticles;
(3) separating the microparticles from the emulsion obtained in (2);
(4) washing the separated microparticles obtained in (3) to neutral pH;
(5) adding the washed microparticles obtained in (4) into a solution of metal ions to form a mixture, the concentration of the metal ions in the mixture being in a range of 100-1000 mg/L;
(6) shaking the mixture obtained in (5) so as to allow the microparticles to adsorb the metal ions; and
(7) drying the shaken mixture obtained in (6) so as to obtain the nanoparticles of glucidamin that are loaded with metal ions.

5. The preparation as claimed in claim 4, wherein said solution of metal ions is at least one solution of sulphate, hydrochloride or nitrate of said metal ions.

6. The preparation as claimed in claim 4, wherein said diluted acid solution is acetic acid or hydrochloric acid.

7. The preparation as claimed in claim 4, wherein a particle diameter of each of said nanoparticles is in a range of 5-500 nm.

8. The preparation as claimed in claim 1, wherein the amount of free amino groups in the glucidamin is in a range of 90%-100% based on the total amount of amino groups in the glucidamin.

9. The preparation as claimed in claim 4, wherein the amount of free amino groups in the glucidamin is in a range of 90%-400% based on the total amount of amino groups in the glucidamin.

* * * * *